United States Patent
Heiter

(10) Patent No.: US 10,940,032 B2
(45) Date of Patent: Mar. 9, 2021

(54) DEVICE FOR TREATING CARPAL TUNNEL SYNDROME OF A PERSON'S HAND

(71) Applicant: CURMED GMBH & CO. KG, Villingen-Schwenningen (DE)

(72) Inventor: Uwe Heiter, Villingen-Schwenningen (DE)

(73) Assignee: CURMED GMBH & CO. KG, Villingen-Schwenningen (DE)

( * ) Notice: Subject to any disclaimer, the term of this patent is extended or adjusted under 35 U.S.C. 154(b) by 387 days.

(21) Appl. No.: 15/739,595

(22) PCT Filed: Jun. 20, 2016

(86) PCT No.: PCT/EP2016/064149
§ 371 (c)(1),
(2) Date: Dec. 22, 2017

(87) PCT Pub. No.: WO2016/207100
PCT Pub. Date: Dec. 29, 2016

(65) Prior Publication Data
US 2018/0161190 A1     Jun. 14, 2018

(30) Foreign Application Priority Data
Jun. 22, 2015   (DE) ...................... 20 2015 103 260.9

(51) Int. Cl.
*A61F 5/01*      (2006.01)
*A61F 5/34*      (2006.01)

(52) U.S. Cl.
CPC ............ *A61F 5/0118* (2013.01); *A61F 5/012* (2013.01); *A61F 5/34* (2013.01); *A61F 2005/0167* (2013.01)

(58) Field of Classification Search
CPC .......... A61F 5/0118; A61F 5/012; A61F 5/34; A61F 5/05841; A61F 5/05866;
(Continued)

(56) References Cited

U.S. PATENT DOCUMENTS 3,010,452 A * 11/1961 Smith ..................... A61F 5/373
                                                        128/881
3,027,895 A *  4/1962 Williams .............. A61F 5/3761
                                                        128/878
(Continued)

FOREIGN PATENT DOCUMENTS

DE     4326751        2/1995
EP     2060244 A1     5/2009
(Continued)

OTHER PUBLICATIONS

International Search Report: PCT/EP2016/064149 dated Sep. 29, 26.
(Continued)

*Primary Examiner* — Rachael E Bredefeld
*Assistant Examiner* — Camtu T Nguyen
(74) *Attorney, Agent, or Firm* — Muncy, Geissler, Olds & Lowe, P.C.

(57) ABSTRACT

A device for treating carpal tunnel syndrome of a person's hand, which has a palmar aspect, with thenar and hypothenar regions, and a dorsal aspect opposite the palmar aspect. The cuff has a C-shaped profile in cross section, wherein two ends of the C-shaped profile of the cuff form the cuff opening. The cuff is formed from two or more cuff parts, wherein these cuff parts have a C-shaped profile in cross section and are connected to each other by means of a connection element to form the cuff. The cuff parts are preferably connected to each other, by means of the connection element, in a movable and/or pivotable and also releasable manner, such that the width of the cuff opening can be individually adapted for each patient. This results in simple, efficient and safe treatment and handling of the cuff according to the invention or of the device.

15 Claims, 9 Drawing Sheets

(58) Field of Classification Search
CPC .......... A61F 5/05858; A61F 2005/0167; A61F 13/00004; A61F 2013/00093; A61F 5/0585; A61F 5/05875; A61F 5/3723; A61F 5/373

See application file for complete search history.

(56) References Cited

U.S. PATENT DOCUMENTS

| | | |
|---|---|---|
| 5,772,620 A | 6/1998 | Szlema et al. |
| 6,146,347 A | 11/2000 | Porrata |
| 6,808,501 B2 | 10/2004 | Stess et al. |
| 7,175,603 B2 | 2/2007 | Fritsch et al. |
| 2004/0210169 A1 | 10/2004 | Hepburn et al. |
| 2010/0298750 A1 | 11/2010 | Chiang et al. |

FOREIGN PATENT DOCUMENTS

| | | |
|---|---|---|
| EP | 2664306 A1 | 11/2013 |
| RU | 102886 U1 | 3/2011 |
| WO | WO03/007804 A2 | 1/2003 |
| WO | WO03/017885 A1 | 3/2003 |
| WO | WO03/017886 A1 | 3/2003 |

OTHER PUBLICATIONS

Notification Concerning Transmittal of Internaitional Preliminary Report on Patentability (Chapter I) and English Translation of Written Opinion pf the International Searching Authority dated Jan. 4, 2018.

Claudia Lemper et al., "BARMER GEK Devices for Healing and Aids Report 2012", pp. 1-214, Sep. 2012.

* cited by examiner

DEVICE FOR TREATING CARPAL TUNNEL SYNDROME OF A PERSON'S HAND

This nonprovisional application is a National Stage of International Application No. PCT/EP2016/064149, which was filed on Jun. 20, 2016, and which claims priority to German Patent Application No. DE 20 2015 103 260.9, which was filed in Germany on Jun. 22, 2015, and which are both herein incorporated by reference.

BACKGROUND OF THE INVENTION

Field of the Invention

The present invention relates to a compression syndrome of the median nerve in the area of the carpal tunnel, which runs along the palmar aspect or palm side of the wrist. Typical symptoms are occurring pain or discomfort that may radiate from the hand to the entire arm. In advanced stages, it can lead to muscle wasting in the area of the ball of the thumb, weakness when grasping and a loss of sense of touch. Surgical therapy is associated with the risks and complications of a surgical procedure.

Description of the Background Art

It is known to treat carpal tunnel syndrome in a conservative manner. In this case, wearing special night splints or applying molded support bandages can eliminate or at least mitigate the discomfort for a while. This is done by so-called wrist orthoses which prevent pain-causing bending of the wrist, particularly at night. These orthoses or respective bandages reduce the pain but do not produce sufficient therapeutic effect and therefore do not fight the cause of the pain, as set out in the BARMER GEK Devices for Healing and Aids Report 2012 by Claudia Lemper et al. dated September 2012. Such wrist orthoses are known, for example, from U.S. Pat. No. 7,175,603 B1 and the patent applications EP 2 060 244 A1, DE 43 26 751 A1 and US 2010/0298750 A1.

An alternative to these wrist orthoses are special splints that open the carpal tunnel of the hand by stretching the latter, thereby extending the transverse bands.

This process reduces the pressure on the nerves, reducing pain and allowing the inflammation to heal.

Patent application WO 03/017885 A1 describes an automatic device and a method for treating carpal tunnel syndrome, which comprises a housing for receiving the patient's hand, having pressure elements that are in contact with the hypothenar region or the palm on the little finger end, the thenar region or the palm on the thumb side, and the dorsal region or the back of the hand. The housing for receiving the hand is a closed housing in a O-shape with a hole for the thumb. Because of this, it is unfortunately necessary that two active pressure sources apply pressure: for the first pressure element, on the hypothenar region, and for the second pressure element, on the thenar region. On the opposite dorsal aspect of the hand, a pressure pad provides the counter pressure. Here, the control unit controls the two active pressure sources such that the thenar and hypothenar regions of the hand are pulled apart and around the dorsally arranged pressure pad. Only as a result of the two forces acting on the palmar aspect and a force in the dosed housing acting on the dorsal aspect can a separation of the carpal bone of the hand be achieved. In this case, the housing must be measured and made to fit the size of the hand to be treated very precisely, otherwise there is a reduction in efficiency.

From U.S. Pat. No. 6,146,347 B1 a device and method for treating carpal tunnel syndrome is known. In the patent application WO 03/007804 A2, another device and method for treating carpal tunnel syndrome is disclosed having a C-shaped housing for receiving the right or left hand, with a pressure element in the dorsal region, that has a housing structure open at one end that is necessary for treating carpal tunnel syndrome. This open structure of the C-shaped housing for receiving the right or left hand, as compared to the wrist orthoses that enclose all sides, makes it possible to open the carpal tunnel of the hand by the latter being stretched, thereby extending the transverse ligaments. The pressure element used for this purpose is connected to an active pressure source so that when the hand is inserted into the housing, the pressure element can be activated to exert pressure on the dorsal aspect of the hand. The device includes rigid portions for making contact with the thenar and hypothenar regions of the hand. By means of the one downward force of the pressure element and the lever action of the rigid portions, the carpal bone is stretched. Here, it is necessary to measure and shape the housing such that the patient's hand can be effectively received and can be treated by precisely controlled transverse stretching. Because of its rigid material structure, the housing must therefore be produced in the different sizes S (small), M (medium) and L (large). By measuring the width of the hand, the size that is suitable for each patient is determined. Using the correct size of the housing is a decisive factor for the chances of successful treatment. If the housing is too narrow, the hand to be treated is compressed and cannot be sufficiently depressed by the pressure element. This reduces the degree of effectiveness because the carpal tunnel is insufficiently stretched. Despite accurate instructions on how to measure the width of the hand, this method is highly susceptible to false measurements. This in turn results in a comparatively high proportion of returned or exchanged devices. How many patients perform the treatment with a cuff suitable for them can be determined only with difficulty.

In the European Patent EP 2 664 306 B1, a device for treating carpal tunnel syndrome with a C-shaped housing for receiving the right or left hand is disclosed, having a pressure element in the dorsal portion. This open structure of the C-shaped housing for receiving the right or left hand makes it possible, as compared to the wrist orthoses that enclose all sides, to open the carpal tunnel of the hand by the latter being stretched, thereby extending the transverse ligaments. This device allows for a differentiated treatment in that inserts of two different strengths can be added to the cuff, which allow the patient to adjust or decrease the size of the cuff. Along with a uniform, C-shaped and one-piece cuff, the patient receives a set of inserts of different strengths and colors. The patient no longer needs to determine the right cuff size by measuring his palm. The inserts of varying strengths included allow the patient to independently adjust the appropriate size by trial and error and to modify it by exchanging/removing the inserts if necessary. Using the cuff is thus advantageously simplified for the patient and he is always given the correct size. Logically, this device proves difficult to use for the patient due to the having to choose from the various inserts.

SUMMARY OF THE INVENTION

It is therefore an object of the present invention to provide a device for treating carpal tunnel syndrome, and a cuff for a device for treating carpal tunnel syndrome, which can be used in a convenient, controlled and efficient manner.

The inventive solution is to design the cuff for a device for treating carpal tunnel syndrome of a person's hand, having a palmar aspect with thenar and hypothenar regions and a dorsal aspect opposite the palmar aspect and being formed in cross section as a C-profile, out of two or more cuff parts. The unilaterally open structure of the C-shaped cuff for receiving the right or left hand, as compared to the wrist orthoses that enclose all sides, makes it possible to open the carpal tunnel of the hand by stretching it, thereby extending the transverse ligaments and thus providing targeted treatment of the cause of carpal tunnel syndrome and not just addressing the symptoms.

The cuff parts all show, or at least partially show, a C-shaped profile in cross section and can be interconnected by at least one connection element to the cuff that is C-profile-shaped in cross section. The cuff parts are joined together in such a way that the connected cuff is suitable for providing counter support for an inserted pressure pad and for opening the carpal tunnel of the hand by stretching it, thereby extending the transverse ligaments and thereby providing targeted treatment of the cause of carpal tunnel syndrome and not just addressing the symptoms. The cuff parts are also interconnected such that they have a patient-appropriate cuff opening and a corresponding patient-appropriate, differentiated cross section, independent of the connection. Thereby, it is in particular possible that by connecting the C-shaped cuff portions, a different opening with a different cross section for receiving a person's hand suffering from carpal tunnel syndrome is created. By means of this preferred adjustment approach using the connection element, a very simple, reliable and convenient way of providing efficient treatment of carpal tunnel syndrome of a patient is made possible, and of adapting the cuff to the needs of the patient. Due to the multi-part design of the cuff parts of the cuff, in connection with the ability to individually adjust the cross section of the associated opening for the hand by means of the connection element or the connection elements, it may often even be possible that there is no need to provide an insert in the cuff, as per the prior art.

A cuff that is particularly easy to use for treating carpal tunnel syndrome has two cuff parts, which are formed C-shaped in cross section and can be connected by the inventive connection element to an inventive cuff that is C-shaped in cross-section. These two cuff parts prove to be particularly advantageous since the acceptance and handling by the patient in terms of adjusting and connecting the cuff parts to the cuff is given in a particularly advantageous manner.

It has proven to be especially advantageous to form the connection element such that the associated cuff parts are moveable or pivotable relative to each other, and thus an adjustment of the width of the cuff opening of the C-shaped cuff and thus a widening or a reduction of the cross sectional opening of the cuff to meet the individual needs of the patient is given. By providing an adjustment of the connection by means of shifting, which occurs both by way of a shifting along a linear line or along a slightly curved, in particular circular curved line, a very simple and safe adjustment and handling of the cuff with regard to meeting individual needs is established. The same goes for an adjustment of the width by a pivoting motion, wherein the two cuff parts are pivoted with respect to one another about a fixed or sliding axis on a cuff part, and the width of the cuff opening can be modified and adapted to the needs of the patient.

In particular, a variety of intermediate positions can be utilized for individual adjustment. In this case, individual positions are marked particularly by latching elements so that unintentionally leaving the desired shifting, pivoting or connection position is impeded without excluding or preventing a simple, convenient and safe adjustment.

It has also been proven, in addition to providing a plurality of preferred intermediate positions, to make it possible to select any intermediate position from the continuously connected intermediate positions of the shifting path and/or the pivoting positions, and to connect these in this position by means of the movable and/or pivotable connection element and to hold these in place.

The arrangement of one or more connection elements in sections of the cuff parts, which mutually overlap, has proven particularly useful since there, a simple and efficient connection by means of the one or more connection elements is provided. This is all the more efficient, the less curved the overlapping sections with the connection elements are formed. Flat overlapping surfaces have proven particularly advantageous since they can be very easily and reliably slide on top of each other, thus creating a very reliable connection by means of the one or more connection elements.

As an alternative to the flat overlapping portions, cylindrically curved surfaces have also been proven which can be moved relative to one another by means of a pivoting movement and thus can be securely connected by means of a connection element. Particularly with the same or slightly different cylinder radii, this is possible in a very reliable manner. The cylindrically curved surfaces of the overlapping sections allow for an inventive cuff with a C-shaped cross section, which proves to be particularly easy to handle. Even minor deviations from a constant cylinder radius show no significant limitation of the positive effects. The flat or slightly cylindrically curved, overlapping sections can be used particularly well by a patient for adapting to individual needs.

If the device according to the invention is to have a pressure pad which is inserted into the cuff, it has proven particularly useful to provide at least one connection element of the inventive cuff, having a plurality of openings for receiving a hose for filling or emptying a fluid for the pressure pad, that is inserted in the cuff. In this case, at least one opening in the area of the connection element is formed as a slot so that the two cuff parts overlapping in the area of the connection element can be moved relative to each other, and that thereby according to the invention, the width of the cuff opening or the cross section of the cuff can be designed to be adjustable, without a hose inserted in the overlapping openings of the connection element being sheared off or jammed. The slot ensures the movement of the cuff parts provided according to the invention by the slidably designed connection element in a particularly advantageous manner. By carefully choosing the length of the slot, the degree of individual adjustment of the possible shifting path and/or pivoting range of the cuff parts relative to each other, and thus the extent of the width of the cuff opening, can be advantageously defined and can vary in this area. This makes handling the inventive cuff advantageously limited, thereby precluding improper handling, e.g., improper joining of the cuff parts by means of the connection element.

It has proven to be especially advantageous to provide cuff parts with guide elements for defining the possible shifting and/or pivoting of the cuff parts relative to one another. This way, a specified shifting and/or pivoting of the cuff parts relative to one another is set for a limited geographic area and also guaranteed for a less experienced patient, thereby largely precluding improper handling.

Connection elements such as tongue and groove connections, slide guides and/or edge guides have proven to be particularly preferred guide elements. However, the guide elements are not limited to the guide elements specifically mentioned here. Besides being able to provide a single, connected pair of guide elements, it has proven particularly advantageous to provide two or more, particularly mutually parallel pairs of particularly identical guide elements. These ensure particularly reliable guidance during the shifting and/or pivoting process and thus the ability to individually adapt to the needs of the individual patient by reducing the risk of tilting, thus largely preventing blockage of the cuff parts during individual fitting.

Especially the provision of a pair of guide elements in the manner of a tongue and groove connection, wherein the spring is movably guided along the groove, thereby preventing lateral sliding of the spring from the groove, demonstrates the beneficial effect. Correspondingly, it has proven beneficial to develop a slide guide from a pair of guide elements, in which a sliding block is run in a slide guide, thereby achieving positive guidance along the slide track. Alternatively, it has proven effective to provide a so-called edge guide, wherein two opposite edges of a cuff part are laterally guided by guide elements. These are formed particularly as pins or projections, which rise from the corresponding cuff part. They prevent a lateral shifting of the cuff parts relative to one another in that these guide elements positively guide the edge in the manner of a sideward lateral stop, ensuring longitudinal guiding. In addition, by providing vertical stops, the edge guide can also prevent unintentional vertical sliding of one cuff part out from the other connected cuff part. These guide elements have proven particularly useful since they ensure a very defined ability of individual positioning the cuff parts relative to one another and thus an adjustment of the width of the cuff opening in a simple and efficient manner. Improper handling is therefore less likely.

In a particularly advantageous embodiment of the inventive cuff, guide elements are designed as one or more slide guides in which one or more sliding blocks engage with an undercut in one or more sliding tracks, wherein the profile of the sliding blocks corresponds to the profile of the associated sliding track. Thus, apart from the lateral guide, unwanted vertical sliding out of the sliding blocks from the sliding track, which together constitute a guide element, is curtailed or precluded. Due to the unchangeable shape of a sliding block and the uniform design of the sliding track, it is advantageously ensured that the cuff parts connected via the slide guide are inseparable and that thus the functioning of the cuff is guaranteed even under extreme conditions.

According to the invention, a separation area is additionally provided in the sliding track, which enables removal and or insertion of the profiled sliding block out of or into the profiled sliding track. This is achieved in particular in that the profiled sliding track no longer conforms to the profile of the sliding block in the separation area but instead has a recess through which the sliding block can be removed from, or inserted into, the sliding track. This enables complete separation or merging of the cuff parts with the guide element, which is formed as a part of the connection element as a sliding block having an associated sliding track. This ensures good handling, which is characterized by simple and reliable guidance, as well as particularly good productivity of the individual parts as part of the cuff.

The separation area is preferably designed such that it corresponds in shape to the sliding block, wherein the size of the separation area is preferably selected such that the recess is selected to be somewhat larger than the size of the sliding block. In addition, the shape of the recess of the separation area is preferably selected such that it matches the shape of the sliding block, providing a preferred direction during insertion or removal of the sliding block from the sliding track and thus providing a defined orientation of the two cuff parts when connecting or separating, as well as safe and correct handling. This is in particular achieved in that a rotation-invariant shape of the sliding block, or at least a shape of the sliding block, is chosen that has few preferred directions, i.e., orientations for separating or interconnecting, and thus has a sliding block with few rotation-invariants. This leads to very safe handling in that the connecting or separating of the cuff parts is provided only in the desired, correct and predetermined orientation of the cuff parts relative to one another.

It has proved particularly advantageous to provide one or more cuff parts with a boundary to the shifting and/or pivoting, in particular by means of a stop and/or a sliding track end of a slide guide. This limiting of the shifting and/or pivoting makes it possible to limit the handling of the cuff and thus the adjustment range of the cuff parts relative to each other, thereby defining the functionally and anatomically useful width of the cuff opening without the boundary excluding appropriate cuff openings.

In addition, it has also proven successful to provide the connection element of the mutually movable and/or pivotable cuff parts with a scale to represent a measure of the shifting and/or pivoting or the width of the cuff opening of the cuff. This makes it possible in a particularly advantageous manner to again correctly adapt a successful and proven adjustment of the width of the cuff opening, e.g. after cleaning, disinfection, sterilization or after adjustment and fitting for another patient, and to again make it available to the respective patient. This way, documentation of the treatment, especially in progressive therapies with variable widths of the cuff opening, is possible and the treatment method can be specifically adjusted to the patient and optimized.

The scale is preferably arranged parallel to one or more guide tracks and in particular, the edge of the overlapping areas is provided with a marking which is arranged on or at one of the two overlapping cuff parts and acts as a pointer. The pointer or the marking interacts with the non-overlapped, and thus visible, scale and represents the position and thus a measure for the width of the cuff opening. This type of scale, in particular in connection with the marking on or at the other cuff part, permits particularly reliable reading or adjusting of the width of the cuff opening and thus very safe and reliable therapeutic use of the inventive cuff for treating carpal tunnel syndrome of a hand.

Another preferred embodiment of the invention shows one or more fixing elements, which is or are arranged in or on a connection element. By means of the fixing elements, it is possible to determine the position of the cuff parts in the connected state and to fix the adjusted width of the cuff opening. By arranging the fixing element or elements in a connection element, this fixing can be ensured in a particularly reliable manner, thereby making handling very safe. Exemplary fixing elements such as bolt/nut connections, magnetic connections, adhesive connections, form-locking connections, e.g. latching connections or e.g. hook and loop fasteners (e.g. by means of a Velcro strap) and/or clamping connections, in particular by means of toggle clamps or a combination thereof, have proven successful.

Preferably, the one or more fixing elements are arranged in the area of the guide elements in a connection element so that on the one hand, the adjustment of the width of the cuff opening can be reliably made by means of the guide elements, taking place in particular as a shifting and/or pivoting, and on the other hand, fixing is ensured by means of the fixing elements, which interact in particular with the guide elements.

A particularly preferred fixing takes place by means of a nut/bolt connection, which is arranged in a guide element in the manner of a slot. The bolt provides reliable guidance along the guide element that is designed as a slot. Furthermore, fixing is effected by tightening the nut on the bolt because the cuff parts are pressed onto the guide elements in the connection element, thus being fixed relative to each other.

By means of an alternative, particularly preferred fixing element using a toggle linkage, an easy release by opening the toggle lever and moving and/or pivoting the cuff parts relative to one another can be guaranteed, and by tightening the toggle lever, a tensioning of the cuff parts and thus fixing of these parts relative to one another can be effected. Such a toggle linkage exhibits a lever arm on which a cylinder-shaped end piece is arranged at one end, over the circumference of which the radius of the cylindrical end piece increases. This toggle lever is fastened to the end of a bolt and can be pivoted relative to the bolt end. By pivoting, the distance between the free end of the bolt and the cylindrical end piece of the toggle lever can be varied, either increased or decreased. This makes it possible to adjust a release or tensioning by extending or shortening the free spacing from the free end (cylindrical end piece) and therefore the area where the cuff parts are arranged in the connecting area of the connection elements, releasing these or fixing them relative to one another. Precisely this type has proved particularly advantageous to handle.

Fixing by means of a magnetic connection, adhesive or form-locking connection has also proven to be varyingly advantageous because on the one hand, these are easy to release and again fix, and on the other hand, they can be adapted once to the needs of a single person and can subsequently not be changed, thus being reliably stable. According to need, the appropriate fixing element is chosen as a single component or as a combination of several fixing elements.

A particularly preferred cuff has several guide elements designed as slide guides, having one or more sliding blocks with an undercut and one or more sliding tracks which are provided with a profile that is adapted to the one or more sliding blocks. In the intermediate area between two slide guides, at least one fixing element is arranged. This ensures very safe guidance by enclosing the one or more fixing elements with guide elements and by fixing the cuff parts at different widths.

Particularly preferably, a resilient tab is arranged in the intermediate area, which interacts with a push button of the cuff by means of which the resilient tab can be resiliently shifted and by which the fixing element can be released in the intermediate area, whereby the cuff parts can be moved relative to one another, guided through the guide elements. The resilient tab is preferably formed by slots in one leg of a cuff part in such a way that the area between the slots, which is preferably located in the central area of the cuff, can be resiliently moved or deflected by means of the push button. Preferably, by deflecting the resilient tab, the one or more latching connections, which represent the fixing elements, are brought out of engagement or positive fit so that free movement of the cuff parts relative to one another for adjusting the width of the cuff is made possible. By releasing the push button, the resilient tab springs back and the latching connection again engages form-lockingly so that the width of the cuff and thus the relative position of the cuff parts are fixed relative to each other. This design ensures simple and very safe handling of the cuff according to the invention.

The push button is preferably arranged in the region of an opening formed as a slot in one leg of the cuff part such that the push button can be actuated from the outside by a user, and a shifting and or pivoting of the cuff parts can occur in such a way that the push button can be actuated via the shifting and/or pivoting path, which corresponds to the length of the slot. The push button may thereby be produced as a separate part or as a part that is in particular integrally connected with the resilient tab.

The push button is preferably formed such that it extends through, and preferably beyond, the slot in the region of the resilient tab. This extension makes it possible to implement an additional guide, which forms an additional guide element, thereby ensuring very reliable guidance for the process of moving and or pivoting of the cuff parts relative to one another.

It has been particularly successful to route the hose for supplying or removing a fluid to the pressure pad in the area of this raised push button, in particular through the peripheral region of the push button, thereby protecting the hose from damage in particular due to shearing. The push button is preferably designed flat, large enough and in particular formed with the aid of a depression such that actuation by means of a thumb is reliably ensured. It has been proven to be especially advantageous to design the cuff parts in a mutually releasable manner, and thus mutually separable, and to connect them using one or more connection elements. This type of releasable connection of the cuff parts allows for the individual cuff part to be produced particularly easily, cleaned especially easy and exchanged or replaced if necessary. This provides very reliable handling and adaptability of the cuff to the individual circumstances, in particular when the usual adjustment possibilities by adjusting or shifting or pivoting are not sufficient. For example, by replacing one or more cuff parts of the cuff with a modified connection element or several connection elements, the clearance for an adjustment can be changed, thereby adapting the width of the cuff opening or the opening of the cuff to the vastly different individual needs of different patients.

A particularly advantageous, inventive cuff shows two or more cuff parts with a C-shaped cross section having legs of different lengths. In the connected state, according to the invention, the cuff parts show an overlap of the longer legs and form a connection element, which creates the ability of adjusting the width of the cuff opening, which is limited by shorter legs, and to fix it with the help of one or more fixing elements such that the width remains unchanged during use. The cuff parts are thereby fixed in their position relative to one another by the one or more fixing elements. This is preferably done in the form of a releasable fixing connection, for example, using one of the plurality of bolt/nut connections or one or more of the other aforementioned fixing elements. The leas of the C-shaped cuff parts formed in different lengths provide a cuff that is easy to handle, which, with good adjustability and also good efficiency during use, enables a good insertion of the hand into the cuff and a very advantageous application of force for treating carpal tunnel syndrome.

It has proven to be particularly advantageous to provide, in the central region of the cuff, i.e. in the longitudinal direction of the cuff in the central region, a reinforcement of at least a fixing element, e.g. a latching element, a handle element for handling and/or positioning the cuff parts relative to one another, a guide element and/or a hole for receiving a hose for filling or emptying a fluid for a pressure pad that can be inserted in the cuff. By providing this reinforcement, these elements can be arranged particularly reliably even at a small distance to each other, without significant restriction of adjustability or fixability of the cuffs. With this reinforcement and the arrangement of said elements in the area of the reinforcement, it is ensured that the force acting on the patient's hand necessary for treating carpal tunnel syndrome is sufficient, even if additional, potentially debilitating, elements are provided in the cuff parts.

Using the handle element provided in the central region, the handling of the cuff as a whole or the handling of the individual cuff parts, and thus in particular a relative positioning of the cuff parts to each other and therefore an adjustment of the width of the cuff opening depending on the individual needs of the patient, is made possible in a particularly simple and safe manner. All the more so because the inventive cuff or device for treating carpal tunnel syndrome is handled and adjusted by the patient alone and exclusively with the hand not currently being treated. This is ensured in particular by providing such a reinforcement in the central region, in conjunction with additional elements in this reinforcement region, which facilitate handling.

Moreover, it is advantageous to design the inventive cuff rounded in the area of the edges of the cuff parts, thereby preventing or significantly restricting an undesirable, selective strain on the periphery of the hand. Undesirable pressure by the edges of the cuff parts on the hand can thereby mostly be avoided.

The invention further relates to a device for treating carpal tunnel syndrome of a person's hand, having a cuff, as previously described, and preferably a pressure pad, which is inserted in the cuff and which, in interaction with the other parts of the device, can cause a stretching of the carpal tunnel. With the interaction of the inventive cuff with at least one pressure pad, this device provides particularly reliable and safe handling, thus making good and reliable treatment of the carpal tunnel syndrome of the patient's hand possible.

The invention is explained by way of example below on the basis of preferred exemplary embodiments with reference to the figures. The invention is not limited to these preferred embodiments.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1:
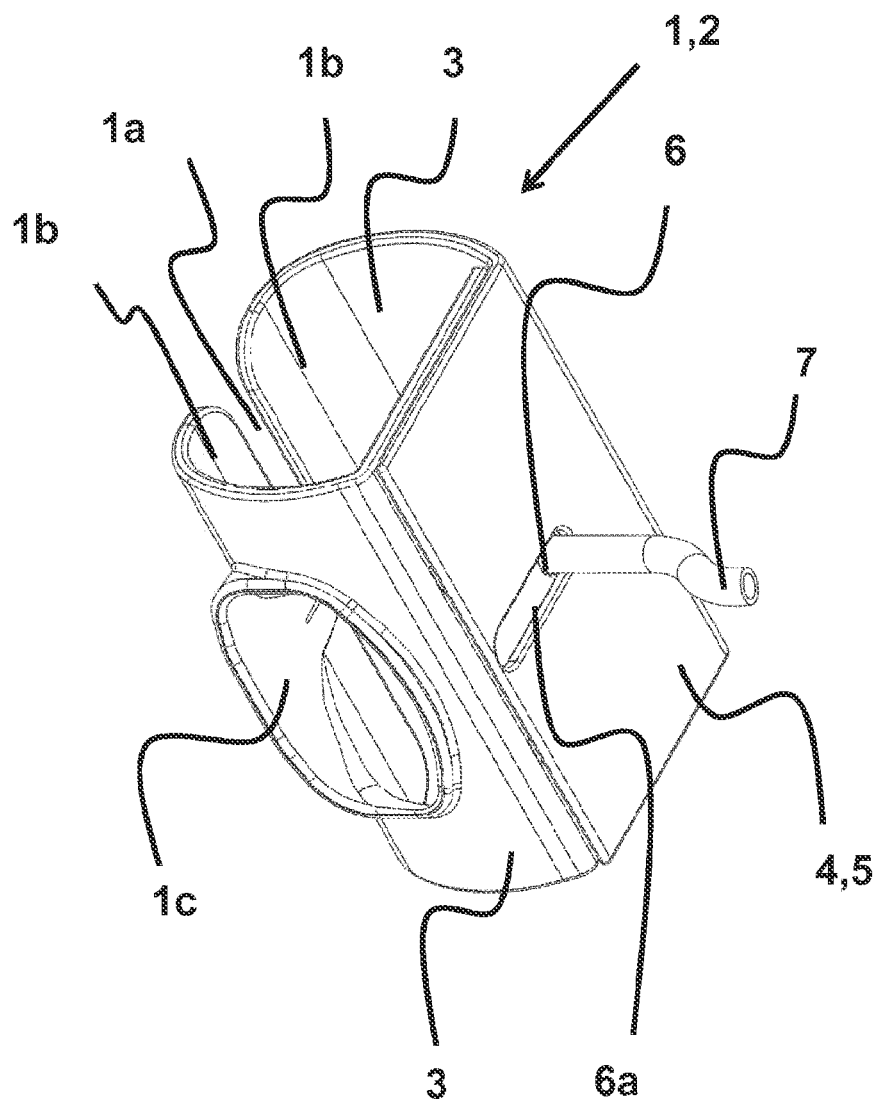
FIG. 1 is an exemplary device for treating carpal tunnel syndrome having a cuff opening with a small width, in a perspective view.

In FIG. 1, a device 2 for treating carpal tunnel syndrome of a person's hand having a cuff 1 with two cuff parts 3 is shown. The two cuff parts 3 have a C-shaped cross section. They overlap in a section 5, in which flat surfaces at least partially overlap. This section 5 forms the connection element 4 of the two cuff parts. Both flat surfaces lie on one another in a partially flat manner. In their center region, i.e., in the longitudinal direction in the center of the cuff parts, in the area of section 5, openings 6 and 6a are located, wherein one of the two openings 6, 6a is formed as a slot 6a. Through these two openings 6, 6a, a hose 7 is inserted from the inside of the cuff 1, by means of which a pressure pad 7a insertable into the cuff 1 can be filled with a fluid or emptied.

A cuff part 3 shows a thumb opening 1c. The cuff 1 shows a hand opening b, through which the patient's hand can be inserted in the dorsal, i.e., in the longitudinal direction, until the thumb protrudes through the thumb opening 1c. The two cuff parts 3 display an overlap 5 with theft one pair of legs 3a and are spaced apart by their other pair of legs 3b such that they form a cuff opening 1a. The width of the cuff opening 1a is dependent on the degree of overlap of the section 5 of the connection element 4 of the two cuff parts 3 of the cuff 1. The two cuff parts 3 C-shaped in cross section are interconnected via the connection element 4 and display such stiffness, that the width of the cuff opening 1a is appropriate for the particular patient, and that a mechanical pressure is produced which pushes the back of the hand (on the dorsal aspect) through and against the open side of the cuff that faces the palm (palmar aspect). The leverage generated by the pressure, which is optionally reinforced by a pressure pad 7a, causes a stretching of the carpal tunnel extending on the palm. The stretching of the carpal tunnel reduces the pressure on the nerves extending therein and relieves the symptoms of carpal tunnel syndrome, constituting a very effective way of treatment. Only by means of the unilaterally open C-shaped cuff does this stretching become particularly effective.

According to the invention, the two cuff parts 3 are moved relative to one another and joined together by means of the connection element 4 in such a way, that the desired width of the cuff opening 1a is fixed, allowing for effective carpal tunnel syndrome treatment for the respective patient.

Figure 2:
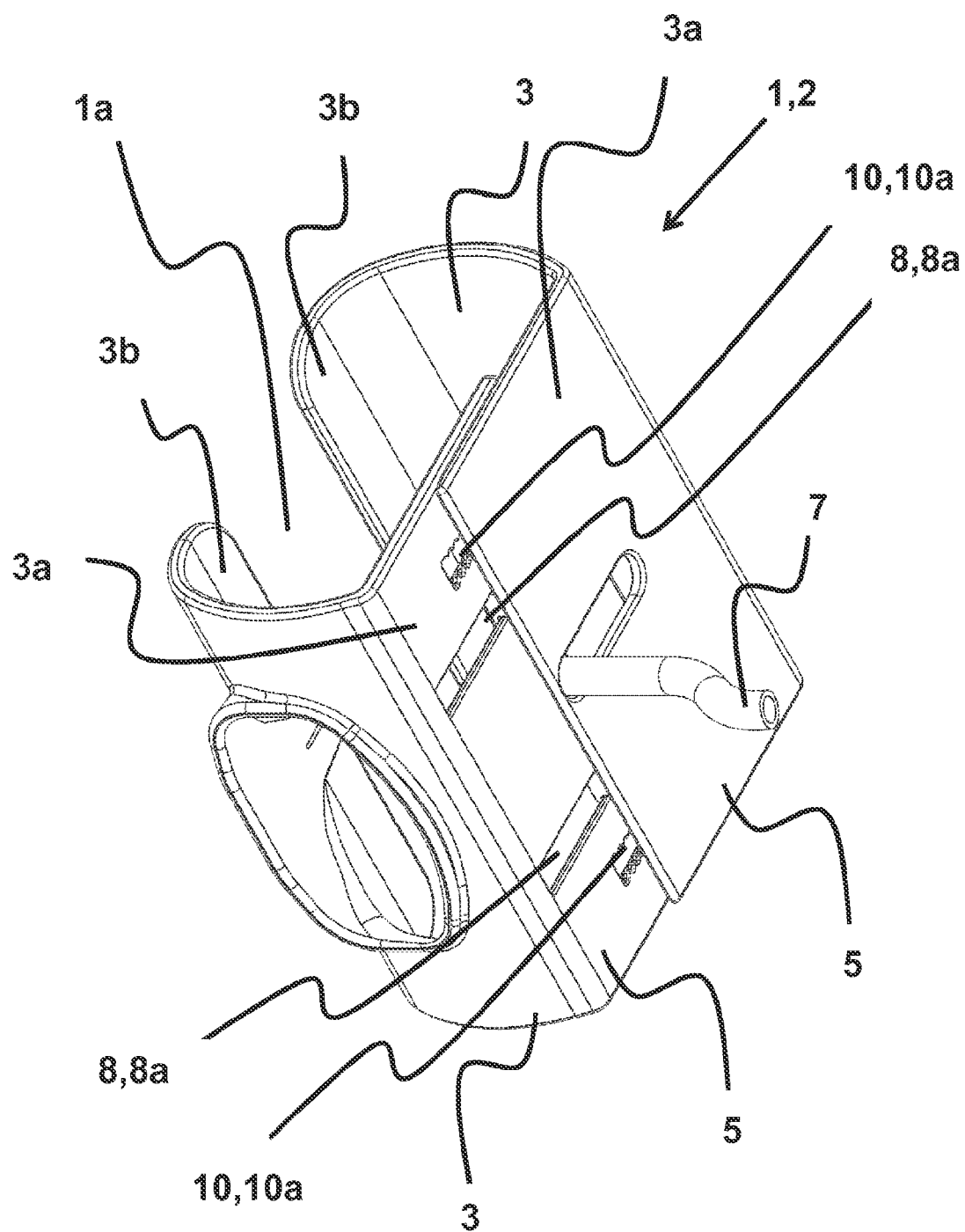
FIG. 2 is the device in FIG. 1 with an expanded width of the cuff opening, in a perspective view.

FIG. 2 shows the same cuff 1 of the device 2 according to the invention, wherein in FIG. 2, the width of the cuff opening 1a is significantly larger than the one selected in FIG. 1. This is achieved by the two cuff parts 3 being positioned to each other such that the overlapping section of theft long legs 3a overlap less than in FIG. 1. This causes the width of the cuff opening 1a to increase.

The connection element 4 of the cuff 1 with the flat sections 5 has two parallel guide elements 8. The two guide elements 8 are formed by a slide guide 8a, said guide elements permitting mutual shifting of the two cuff parts 3a along the slide guide 8a. In each case, a sliding block 8b fixed to a cuff part 3 slides in the sliding track 8c which is formed in the other cuff part 3. The parallel alignment of the two slide guides 8a permits uniform and safe, mutual shifting of the two cuff parts 3a with little tilt.

FIG. 2 additionally displays parallel fixing elements 10, 10a, which are formed in the area of the overlapping flat sections 5, adjacent to the two mutually parallel slide guides 8, 8a. The fixing elements represent latching connections. In these, a shaped block engages in a corresponding latching recess by means of a form-locking connection 10a, thereby preventing a further shift along the slide guide 8a following engagement.

In order to allow a shifting of the cuff parts 3 against each other, first, the fixing element 10, 10a is brought out of engagement in order to subsequently carry out a shift along the slide guide 8a. Once the desired width of the cuff opening 1a is reached, the fixing element 10a is used by again, creating a positive connection by the fixing element 10a, whereby a further shifting of the cuff parts against one another due to the latched fixing is prevented.

In connection with the fixing elements 10, this guiding of the cuff 1 according to the invention by means of the guide elements 8 embodied as a slide guide 8a provides very reliable, safe and easy handling of the cuff 1 or the device 2 for treating carpal tunnel syndrome.

Figure 3:
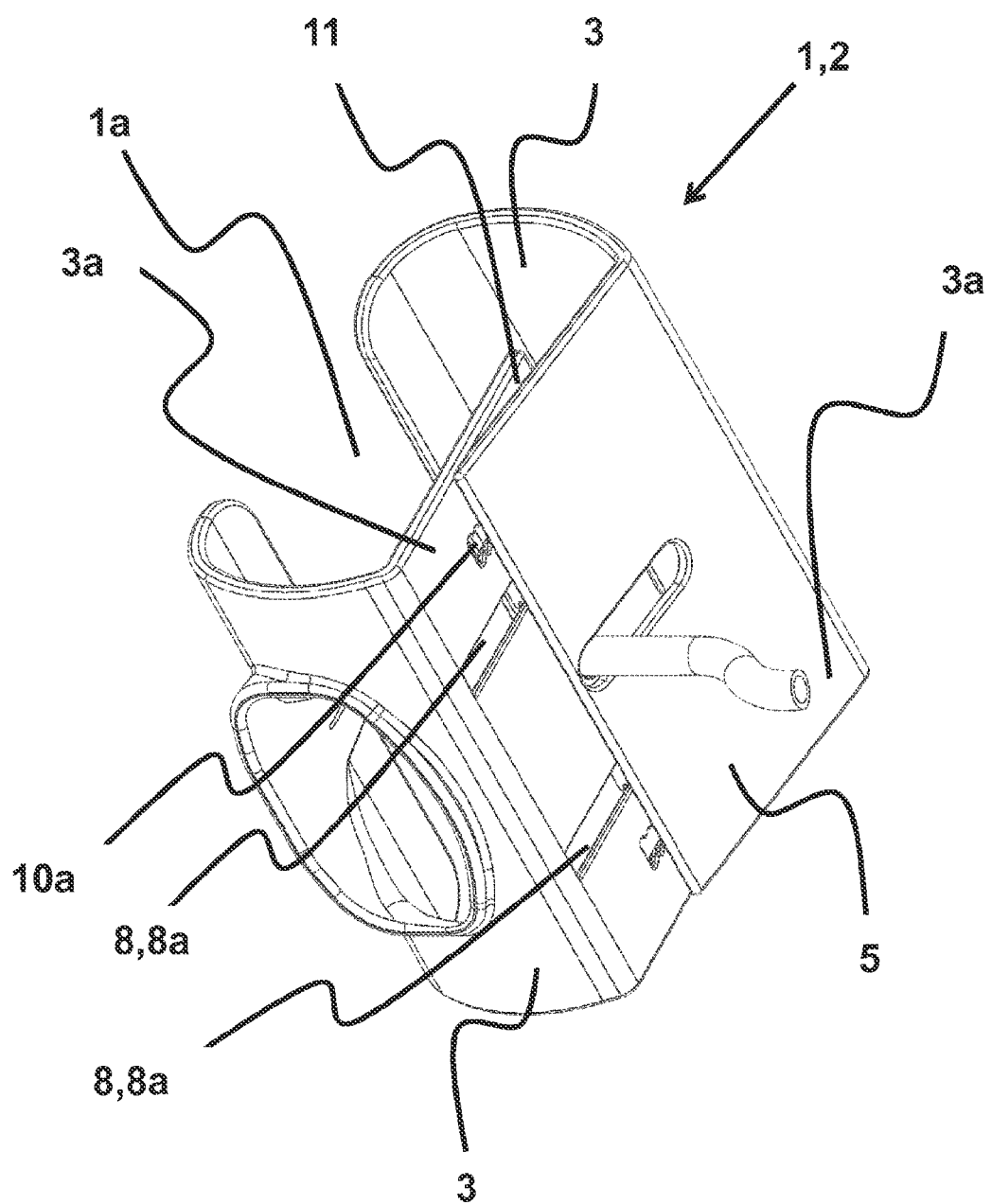
FIG. 3 is the device in FIG. 1 during adjustment of the width of the cuff opening, in a perspective view.

FIG. 3 displays the cuff 1 or the device 2 during adjustment of the width of the cuff opening 1a in a perspective view. In contrast to FIG. 2, in FIG. 3, the one cuff part 3 is tilted against the other cuff part 3. By tilting, the gap 11, which opens over the whole of its length, is created in the region of the overlapping section 5. The form-locking element of the form-locking fixing element 10a is removed from the latching recess through this gap 11, whereby the mobility of the cuff parts 3 in the context of freedom of movement of the slide guide 8a is enabled. The relative ability of shifting the cuff parts 3 against one another is defined by the length of the slide guides 8a. The stop of these slide guides 8a limits the extent of the width of the cuff opening 1a. On the one hand, this defines the lower limit of the width of the cuff opening 1a, and on the other hand, also the maximum width of the cuff opening 1a.

By forming the openings in the flat section 5 that receive the hose 7 as a slot 6a, which corresponds in length to the length of the slide guide 8a, it is ensured that the shift is not limited by the length of the slot 6a, or that by shifting, damage to the hose 7 or a dosing of the hose from the pressing by the long legs 3a, which overlap, is prevented. This ensures in particular the functionality and adjustability of the cuff 1 or the device 2.

Figure 4:
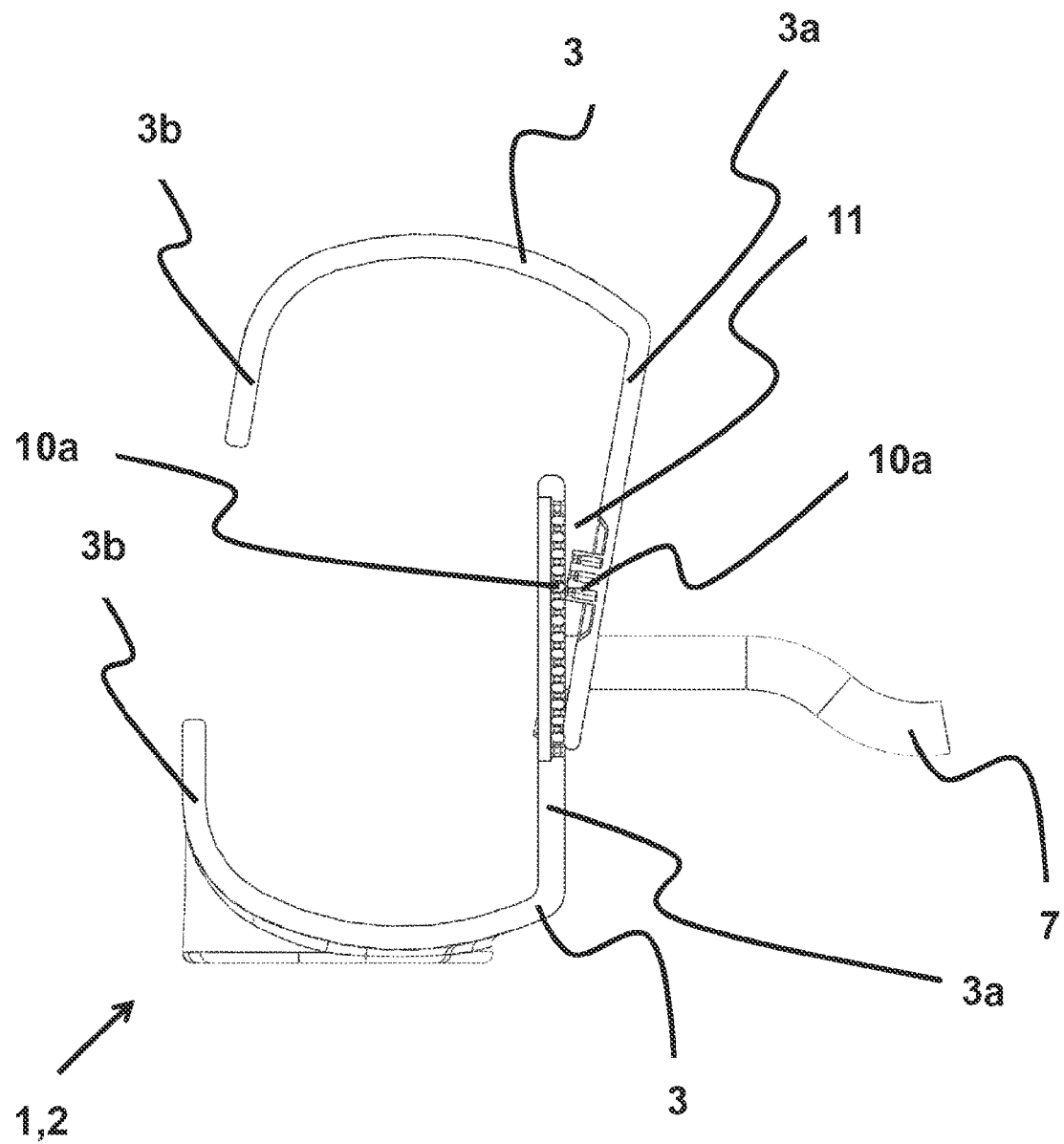
FIG. 4 is the device in FIG. 1 in a cross section through the device according to FIG. 3, in the area of the fixing elements.

FIG. 4 shows the structure of the cuff 1 in a sectional view. The C-shaped cuff parts 3 each show a long leg 3a and a short leg 3b. The long legs 3a show an overlap area (section 5). The cuff parts 3 are tilted against one another so that they show a gap 11 in the overlap area, which opens along its length. In the gap 11, the fixing element 10, 10a is illustrated. It consists of two parts. One part has a characteristic shape and is disposed on the upper long leg 3a. The other part is a recess that can form-lockingly accommodate the first part with the characteristic shape, and due to the positive locking, prevents shifting, i.e., a different positioning of the two cuff parts 3 against one another.

In the scenario shown in FIG. 4, the fixing element 10a is not in engagement so that the cuff parts 3 can be guided to be shifted against each other through the slide guides 8, 8a, which are not shown in FIG. 4.

Figure 5:
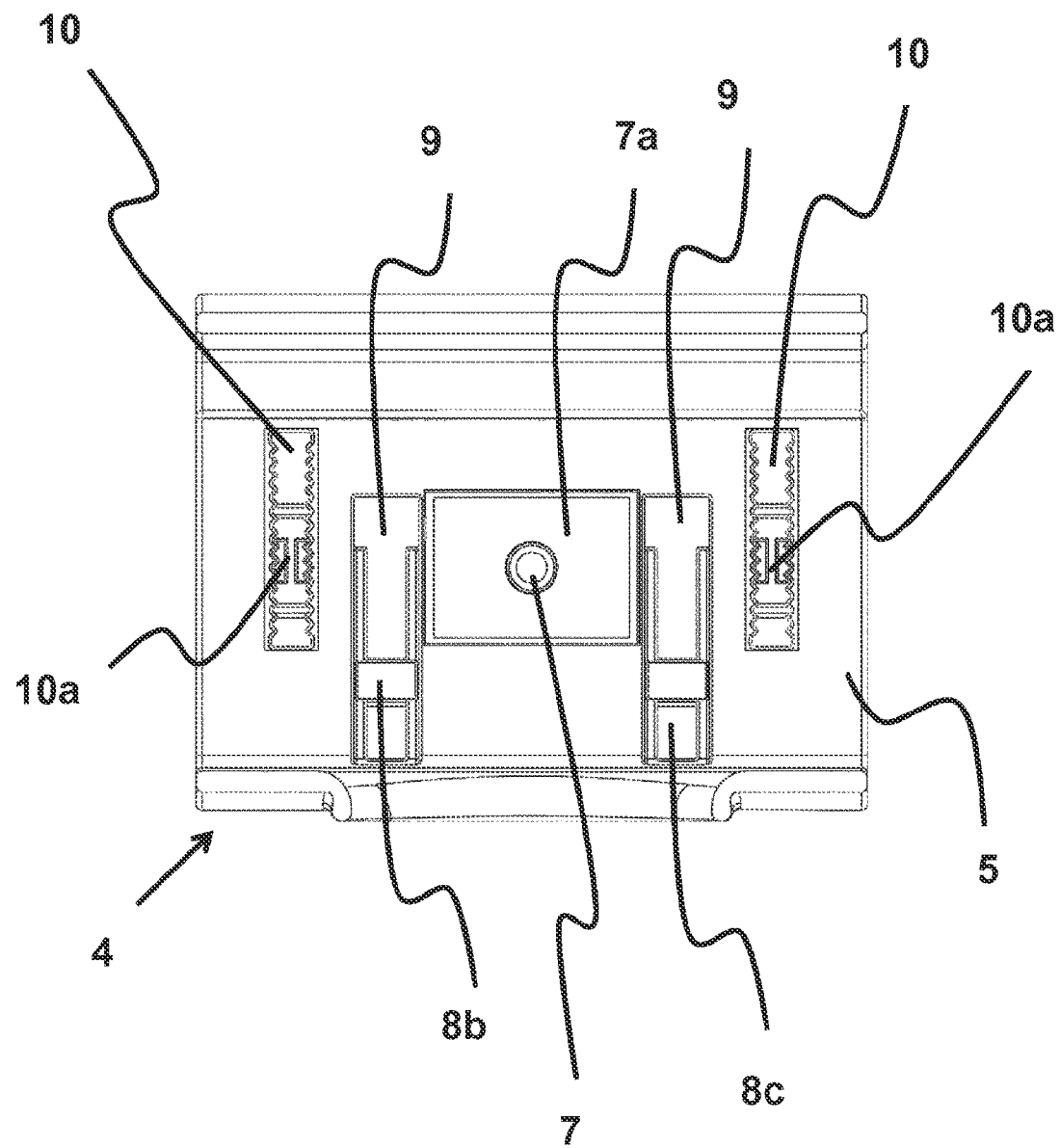
FIG. 5 is the device in FIG. 1 in a horizontal sectional view, through the overlap area of the cuff parts.

FIG. 5 shows the connection element 4 in more detail in a horizontal section in the region of the overlapping section 5. It shows two parallel slide guides 8a with the sliding blocks 8b which have a profile with an undercut and which engage in a sliding track 8c, which correspond to the sliding block 8b in their cross section and provide the ability to be moved safely guided along the sliding track 8c.

The slide guide 8a shows a separating section 9 at one end, which, in line with the other sliding track 8c, does not have a profile with an undercut. Rather, such a separating section 9 has an opening that in its cross section corresponds to the largest cross section of the sliding block 8b. This means that the shape of the separating section typically corresponds to the shape of the sliding block, wherein its size is selected to be somewhat greater. By designing the separating section 9 in such a way, it becomes possible to remove the sliding block 8b from the slide guide 8c, thereby separating, and thus releasing, the two cuff parts 3 from each other. The adjustable connection of the cuff parts 3 of the cuff 1 created by means of this connection element 4 can thereby be released, and a single selective cleaning, maintenance of the individual cuff parts 3, or replacement by another custom cuff part 3, can take place. This creates the ability to ensure handling in a very safe, reliable and permanent manner.

Aside from the two guide elements, which are formed by the sliding blocks 8b and the sliding track 8c and extend parallel to one another, two fixing elements 10a are also disposed in the connection element 4. These have an elongated recess, which is provided with a serrated edge. In this serrated recess, a shaped block engages form-lockingly, which with aid of the positive engagement prevents further shifting of the cuff parts 3 against each other when in the engaged position. To achieve this, the shaped block is arranged on one cuff part 3, and the corresponding form-locking recess is disposed on the other cuff part 3. The fixing using the form-locking fixing elements 10a primarily occurs in the same measure of length as the ability to shift along the guide elements, which are designed here as a slide guide 8a.

In the central area of the connection element 4, the hose 7 is disposed and shown with a pressure pad 7a. By inflating the pressure pad 7a between the back of the patient's hand and the section 5 with the long legs 3a, on the one hand, pressure is created on the back of the hand, and on the other hand, pressure is created towards the inside of the long leg 3a of a cuff part 3 of the cuff 1. This presses the one long leg 3a against the other long lea 3a of the cuff parts 3 in the area of the section 5, and the fixing elements 10a engage or are kept engaged, thereby being protected from accidentally opening.

Figure 6:
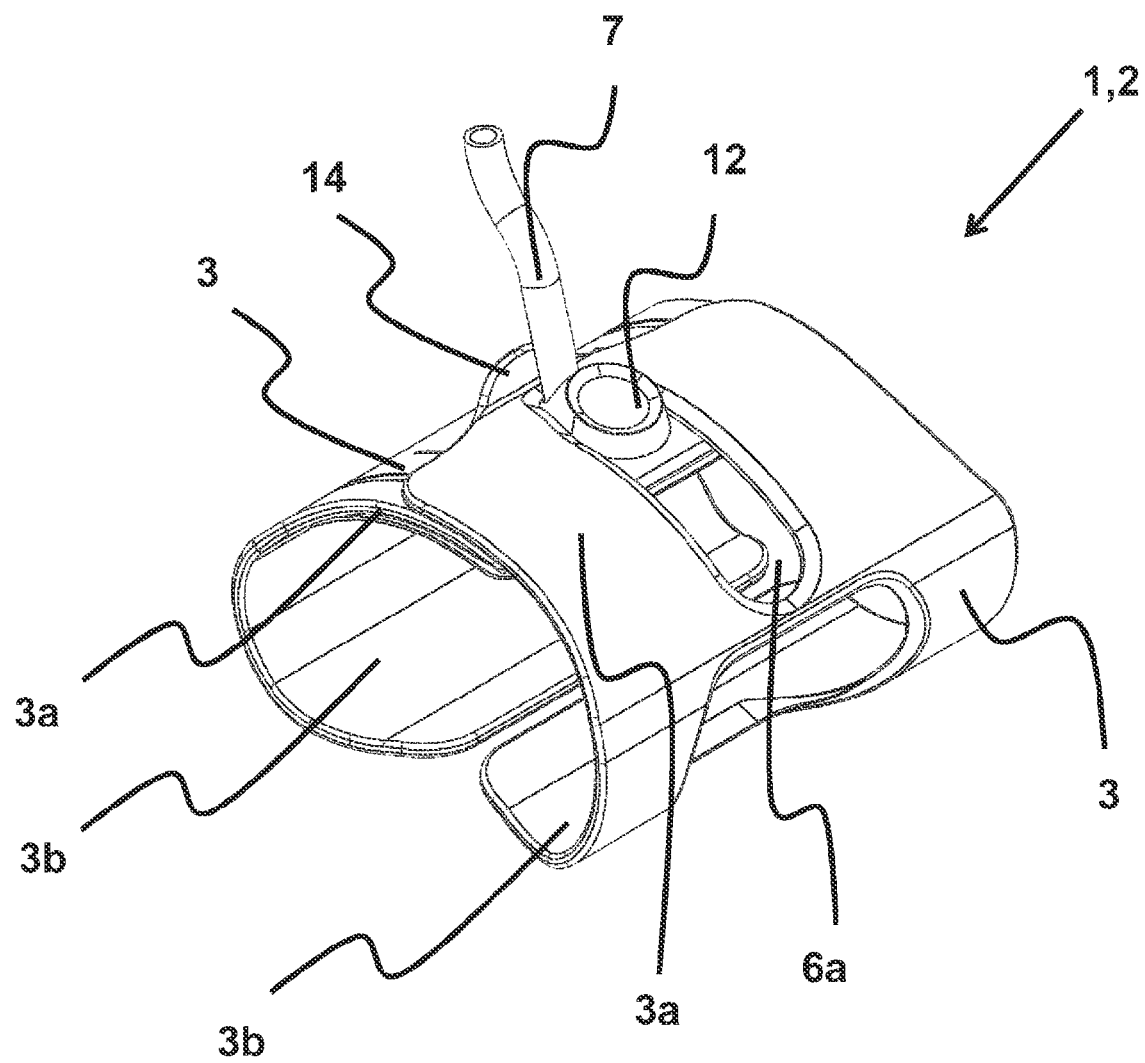
FIG. 6 is another exemplary device for treating carpal tunnel syndrome having a cuff opening with a large width, in a perspective view.

FIG. 6 illustrates another exemplary device 2 for treating carpal tunnel syndrome of a person, having a cuff 1 with two cuff parts 3. The two cuff parts 3 have a C-shaped cross section. They overlap in a section 5, in which cylindrical curved surfaces overlap at least partially. The overlap occurs in the region of the long leas 3a of the cuff parts 3. By mutual shifting, in the manner of a pivoting, the overlap can be increased or reduced, thereby increasing or reducing the width of the cuff 2.

In the central area, as in the device in FIGS. 1 to 5, a slot 6a is located, through which a hose 7 extends for filling or emptying a pressure pad 7a by means of a fluid. Further, the push button 12, which is fixedly connected to the long leg 3a, extends through the slot 6a.

The edges of the cuff parts 3 are formed chamfered, in particular in the area of the slot 6a. In the area of the edge of the outer C-shaped cuff part 3, in the region of the slot 6a in the central region, a handle 14 is provided by means of which the two cuff parts 3 can be mutually positioned in their relative position. Additionally, the handle 14 has a protective function with respect to the hose 7 so that in particular in interaction with the push button 12, it is protected against unintentional kinking and damage.

Figure 7:
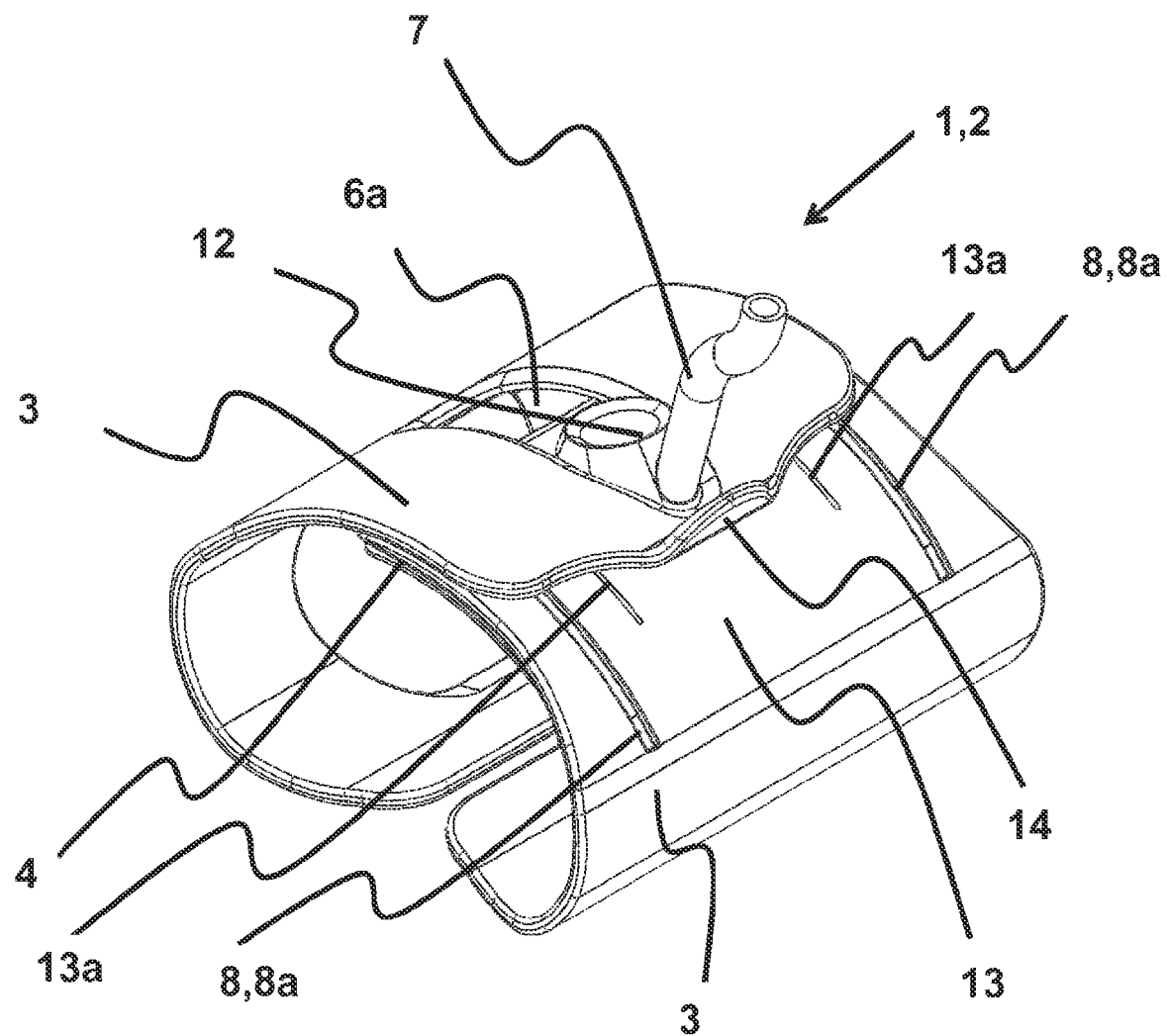
FIG. 7 is the device in FIG. 6, in another perspective view.

The device 1 in FIG. 6 is shown in FIG. 7 in another diagonal view. It represents the structure of the inner cuff part 3. Its long leg 3a shows two guide elements 8 which are designed as slide guides 8a. Between the two, parallel extending guide elements 8, 8a, two slits 13a are arranged, which represent two parallel grooves extending in parallel to the guide elements 8, 8a.

With the help of the slits 13a, a resilient tab 13 is formed in the central area of the long lea 3a. On the top of the resilient tab 13, a push button 12 is arranged, which projects through and significantly beyond the slot 6a. The hose 7 is guided through the edge of the raised push button 12 and is protected by the elevation of the push button 12 as well as by the handle 14. The overlap of the cuff parts 3 is, as shown in FIGS. 6 and 7, small, so that the width of the cuff 1 is large. If the cuff parts 3 are pivoted together along the guide elements 8, 8a after releasing the fixing by pressing the push button 12, the overlap increases and the width of the cuff 1 decreases. This is achieved in that the push button 12 is pressed in the direction of the resilient tab 13, the resilient tab is deflected inwards, and the fixing elements 10, 10a not shown in FIG. 7 are brought out of engagement, thereby making a shifting of the cuff parts 3 relative to one another possible. In order to achieve a fixing of the relative position of the cuff parts 3 to each other, the push button 12 is no longer operated so that by means of the resilient tab 13, the former pivots back resiliently outward into the resting position, and the fixing elements again engage. By means of this positive engagement, the relative position of the cuff parts 3 is fixed.

Figure 8:
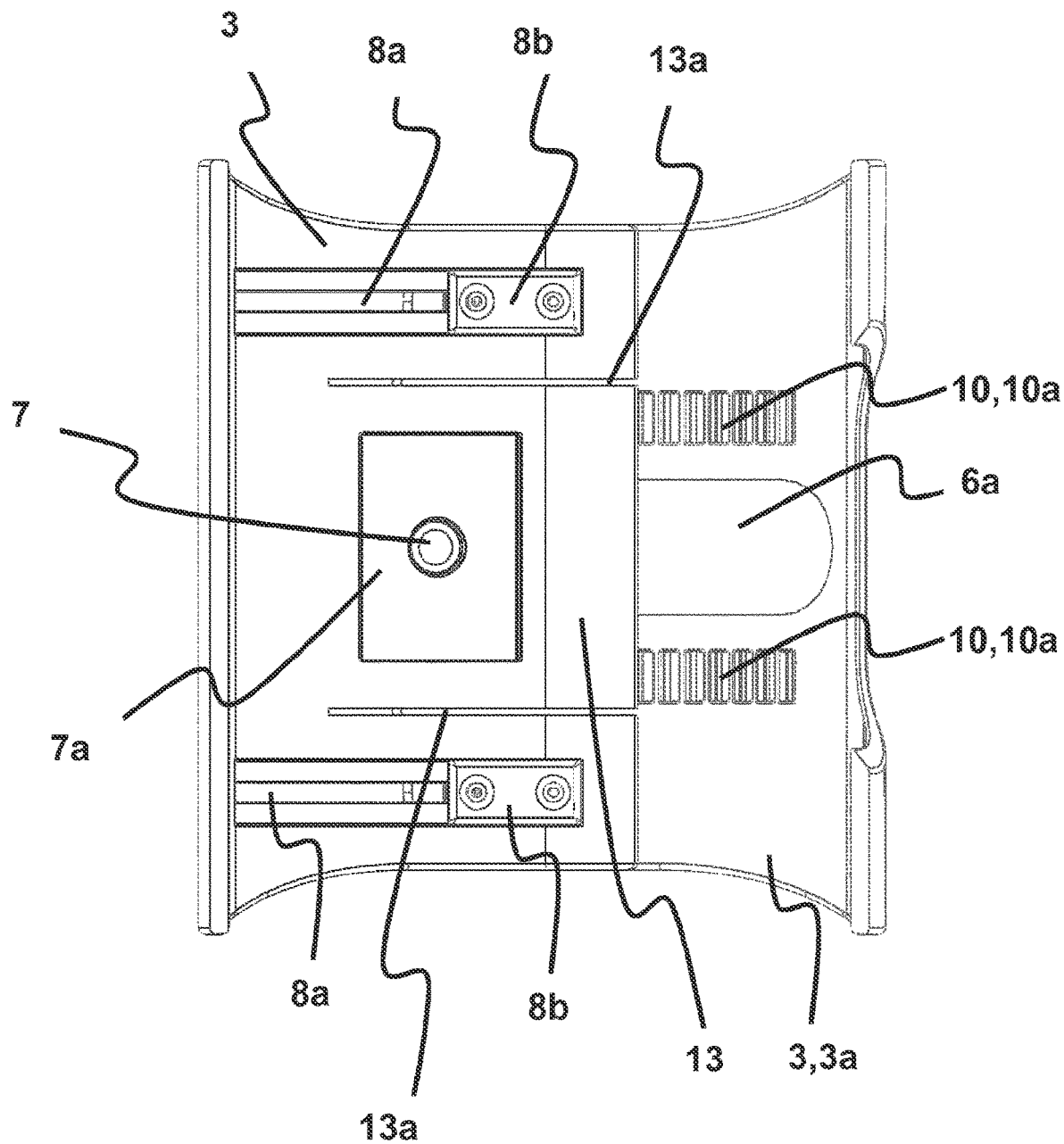
FIG. 8 is the device in FIG. 6, in another perspective view from the inside to the outside.

The bottom side of the two long legs 3a is shown in FIG. 8. The left cuff part 3 shown with the long leg 3a has two parallel sliding tracks 8c. Between these, there are two parallel slits 13a, which form the resilient tab 13 in the central region of the left cuff part 3. By means of the only remaining material connection of the resilient tab 13 with the remaining cuff part 3, a spring bearing is formed, about which the resilient tab 13 can be pivoted. Centrally on the underside of the resilient tab 13, there is the pressure pad 7a, which can be filled or emptied by means of the hose 7. The hose penetrates a substantially circular opening in the resilient tab 13, followed by the slot 6a in the other cuff part 3.

On the averted, upper side of the resilient tab 13 are latching elements which can engage in the form-locking recesses 10a on the inside of the other cuff part 3 and which together form the fixing element 10. The fixing elements 10 are operated by the push button 12 not shown in FIG. 8.

A respective sliding block 8b engages in the sliding tracks 8c, which is firmly connected to the other cuff part 3 and, together with the associated sliding track, forms a slide guide and thus a guide element, which defines and limits the relative movement of the cuff parts 3 to one another. With the sliding blocks 8b and the associated sliding track 8c without a separating section, a permanent connection of the cuff parts 3 with each other is ensured, wherein theft relative position to each other is defined by the interaction of the guide elements 8 and the fixing elements 10.

Figure 9:
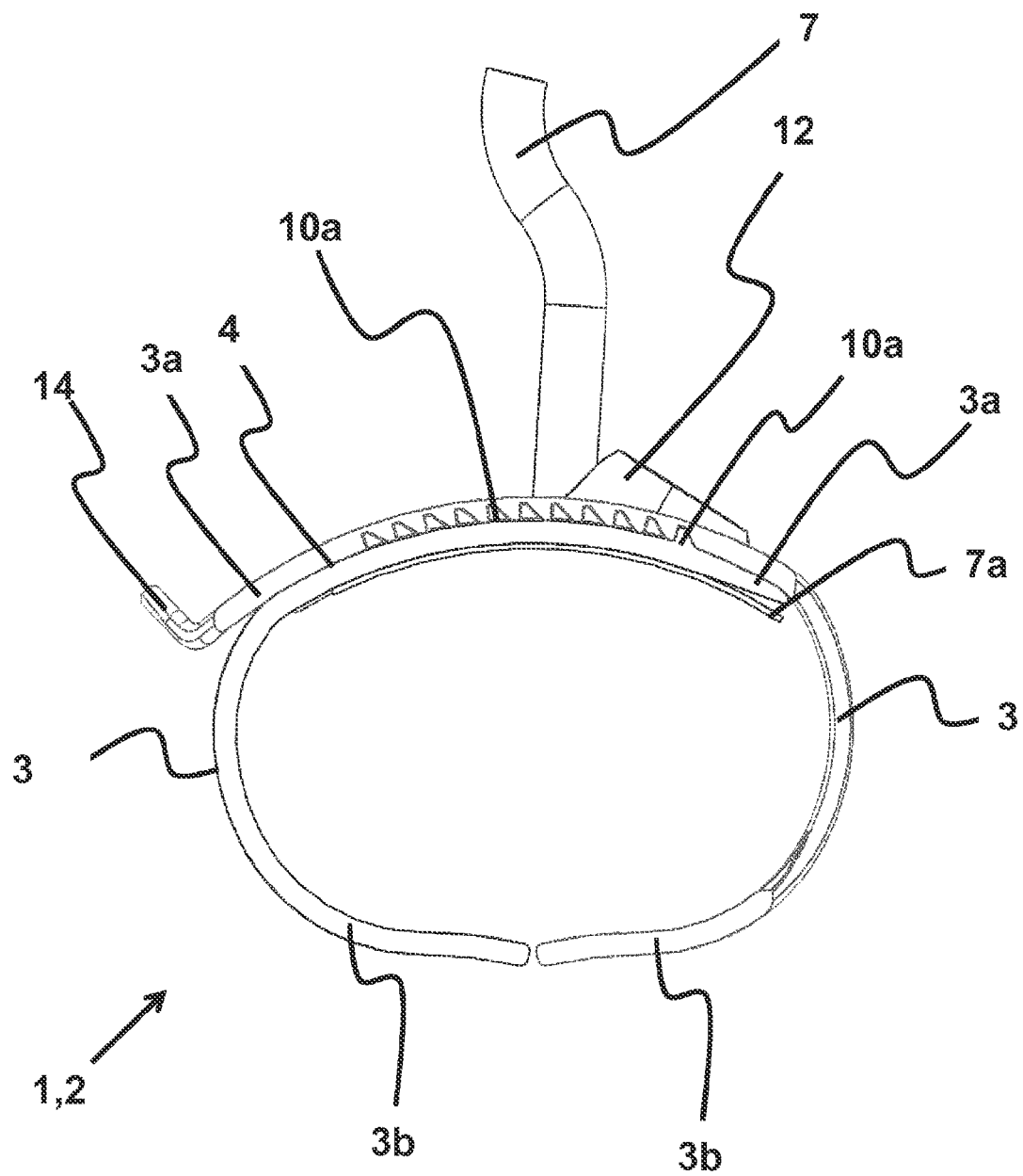
FIG. 9 is the device in FIG. 6 having a small width, in a sectional view through the region of a fixing element.

In FIG. 9, a sectional view taken along the fixing element 10, 10a of the device 2 in FIGS. 6 to 8 is shown in a scenario with a large overlap and thus a small width. The outer long leg 3a of the right C-shaped cuff part 3 shows the handle 14 on its end, and on its inner side, a plurality of form-locking recesses 10a of the latching connections, which, together with the form-locking latching element 10a, form the fixing element 10 designed as a latching connection. The form-locking recesses 10a or the fixing element 10a show two differently steep edges, thereby facilitating an increase in the overlap of the long legs 3a of the cuff parts 3, and making a decrease in the overlap more difficult. By operating the push button 12, the resilient tab 13 is deflected inward with the latching positive-locking fixing element 10a that projects radially outwardly beyond the resilient tongue 13, is removed from the form-locking recess, thus releasing the fixing. A pivoting of the cuff parts 3 can now be done easily in particular by using the handle 14.

On the inner side of the resilient tab 13, the pressure pad 7a is arranged, which can be filled with fluid via the hose 7 such that it increases in thickness and fills the space between the patient's hand and the cuff 1, thereby securing the fixing elements 10 formed as latching connections and the spring force of the resilient tab 13 against unintentional release.

This makes it clear that the adjustability and safety from unintentionally changing the width of the cuff opening a is provided in a particularly advantageous manner, and that thereby, particularly efficient and simple handling of the inventive device or cuff 1 is ensured.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A cuff for a device for treating carpal tunnel syndrome of a person's hand, comprising:
   a palmar aspect with thenar and hypothenar regions; and
   a dorsal aspect opposite the palmar aspect,
   which is formed in cross section as a C-shaped profile,
   wherein opposing ends of the C-shaped profile form a cuff opening,
   wherein the cuff has two or more cuff parts having the C-shaped profile in cross section, two overlapping cuff parts of the two or more cuff parts having overlapping sections that form at least one connection element, the two or more cuff parts being connectable by the at least one connection element, thereby forming the cuff, and the two or more cuff parts are connected in a movable and/or pivotable manner relative to each other for adjusting the width of the cuff opening,
   wherein the at least one connection element has at least two openings for receiving a hose for filling or emptying a fluid for a pressure pad adapted to be inserted in the cuff, and
   wherein the at least two openings are formed through the overlapping sections of the at least one connection element.

2. The cuff according to claim 1, wherein the two or more cuff parts are formed latchingly movable and/or pivotable to one another.

3. The cuff according to claim 1, wherein the the overlapping sections of the at least one connection element have flat overlapping surfaces.

4. A device for treating carpal tunnel syndrome of a person's hand, having a palmar aspect with thenar and hypothenar regions, and a dorsal aspect opposite the palmar aspect, with a cuff according to claim 1, and at least one pressure pad which is inserted in the cuff and which, in interaction with other parts of the device, bring about a stretching of the carpal tunnel.

5. The cuff according to claim 1, wherein said two or more cuff parts are connected with guide elements, said two or more cuff parts pivoting or moving about the guide elements, via one or more tongue and groove connections, slide guides and/or edge guides arranged in said two or more cuff parts.

6. The cuff according to claim 5, wherein the slide guides have one or more sliding blocks with an undercut and one or more sliding tracks with a profile adapted to the one or more sliding blocks, wherein one or more sliding tracks have a separation area, which enables the removal or insertion of the one or more sliding blocks from or into the one or more sliding tracks.

7. The cuff according claim 1, wherein the two or more cuff parts limit the moving and/or pivoting, via a stop or a sliding track end of a slide guide.

8. The cuff according to claim 1, wherein the at least one connection element of the two or more cuff parts has a marking for representing a measure of the width of the cuff opening of the cuff.

9. The cuff according to claim 1, wherein the two or more cuff parts are fixedly connected by one or more fixing elements arranged in the at least one connection element.

10. The cuff according to claim 9, wherein the one or more fixing elements are formed by a bolt/nut connection, a magnet connection, an adhesive connection, a form-locking connection or a clamping connection, or via a toggle clamp.

11. The cuff according to claim 10, wherein a plurality of slide guides formed as guide elements has one or more sliding blocks with an undercut and one or more sliding tracks with a profile adapted to one or more sliding blocks, wherein in an intermediate area between two slide guides, the one or more fixing elements are disposed, wherein in the intermediate area, a resilient tab is arranged, and wherein said cuff is provided with a push button to deflect the resilient tab, the one or more fixing elements being thereby released and the two or more cuff parts mutually shifted.

12. The cuff according to claim 11, wherein the push button is connected with the resilient tab and the push button is arranged and designed such that the push button is operable through an opening formed as a slot and in particular protrudes through it.

13. The cuff according to claim 1, wherein the two or more cuff parts are releasably connected.

14. The cuff according to claim 1, wherein the two or more cuff parts have the C-shaped cross section with legs of different lengths, and the two or more cuff parts have an overlap of the longer legs of different cuff parts for forming the at least one connection element, which is formed with at least one fixing element for a releasable fixing connection of the two or more cuff parts connected by the at least one connection element.

15. The cuff according to claim 1, wherein in a central area of the cuff a reinforcement is designed, comprising at least one fixing element, at least one handle element for handling and/or positioning the connected two or more cuff parts against each other, at least one guide element, at least one latching element and/or at least one hole.

* * * * *